United States Patent
Khan-Sahibzada et al.

(10) Patent No.: US 8,029,471 B1
(45) Date of Patent: Oct. 4, 2011

(54) CIRCULATORY SYSTEM ACCESS PRESERVATION SYSTEM

(76) Inventors: Abdul N. Khan-Sahibzada, Ardmore, OK (US); Donald H. Sheffield, Farmers Branch, TX (US); Thomas G. Fulbright, Keller, TX (US)

( * ) Notice: Subject to any disclaimer, the term of this patent is extended or adjusted under 35 U.S.C. 154(b) by 325 days.

(21) Appl. No.: 11/208,318

(22) Filed: Aug. 19, 2005

Related U.S. Application Data (60) Provisional application No. 60/651,332, filed on Feb. 9, 2005.

(51) Int. Cl.
*A61M 5/178* (2006.01)
(52) U.S. Cl. .................................. 604/164.01
(58) Field of Classification Search ............ 604/167.06, 604/170.01, 170.02, 164.01
See application file for complete search history.

(56) References Cited

U.S. PATENT DOCUMENTS

| | | | |
|---|---|---|---|
| 4,525,157 A * | 6/1985 | Vaillancourt | ................. 604/510 |
| 4,828,547 A | 5/1989 | Sahi et al. | |
| 5,000,740 A | 3/1991 | Ducharme et al. | |
| 5,085,639 A | 2/1992 | Ryan | |
| 5,154,699 A | 10/1992 | Ryan | |
| 5,292,310 A | 3/1994 | Yoon | |
| 5,637,096 A | 6/1997 | Yoon | |
| 6,254,547 B1 | 7/2001 | Phillips | |
| 6,254,574 B1 * | 7/2001 | Burzynski et al. | ....... 604/170.01 |
| 6,267,750 B1 | 7/2001 | Utterberg | |
| 6,511,461 B2 | 1/2003 | Jonsson | |
| 6,589,214 B2 | 7/2003 | McGuckin et al. | |
| 6,786,875 B2 | 9/2004 | Barker et al. | |
| 6,855,128 B2 | 2/2005 | Swenson | |

* cited by examiner

*Primary Examiner* — Theodore Stigell
*Assistant Examiner* — Deanna K Hall (57) ABSTRACT

An access device is disclosed that comprises two main assemblies. The first assembly is the cylindrical cannulation assembly. This is the needle-point-bearing assembly which facilitates cannulation (i.e., insertion of the assembly into the arm of the patient). The cylindrical cannulation assembly comprises a cannulation cylinder which has an insertion point (i.e., the needle puncture point) at a first end. The second main assembly of the invention is the cylindrical conduit assembly. This is the assembly that facilitates fluid flow during treatment free of the worry that the very needle which facilitated access will internally lacerate the blood vessel. The cylindrical conduit assembly comprises a cylindrical conduit which is telescopically positioned within the cannulation cylinder. The cannulation cylinder and cylindrical conduit longitudinally move relative to one another.

12 Claims, 13 Drawing Sheets

Figure 2

ARTERIO-VENOUS GRAFT

CIRCULATORY SYSTEM ACCESS PRESERVATION SYSTEM

CROSS-REFERENCE TO RELATED APPLICATIONS

This application claims the benefit of U.S. Provisional Patent Application No. 60/651,332, filed Feb. 9, 2005 (entitled "A Circulatory System Access Preservation System"), and applicant incorporates the entirety of that provisional patent application herein by reference.

BACKGROUND OF THE INVENTION

An Important Medical Need: Effective Circulatory System Access.

More than eighty percent (80%) of dialysis patients in the United States (e.g., those suffering from end stage renal disease (i.e., kidney failure)) undergo regular hemodialysis treatments.

In order for these treatments to be performed, these patients need an effective blood or circulatory system access, an entry mechanism which allows the blood in the body to be easily taken from an artery or vein (so that it may then be circulated through the dialysis machine) and then be returned to the body through a vein.

Figure 1:
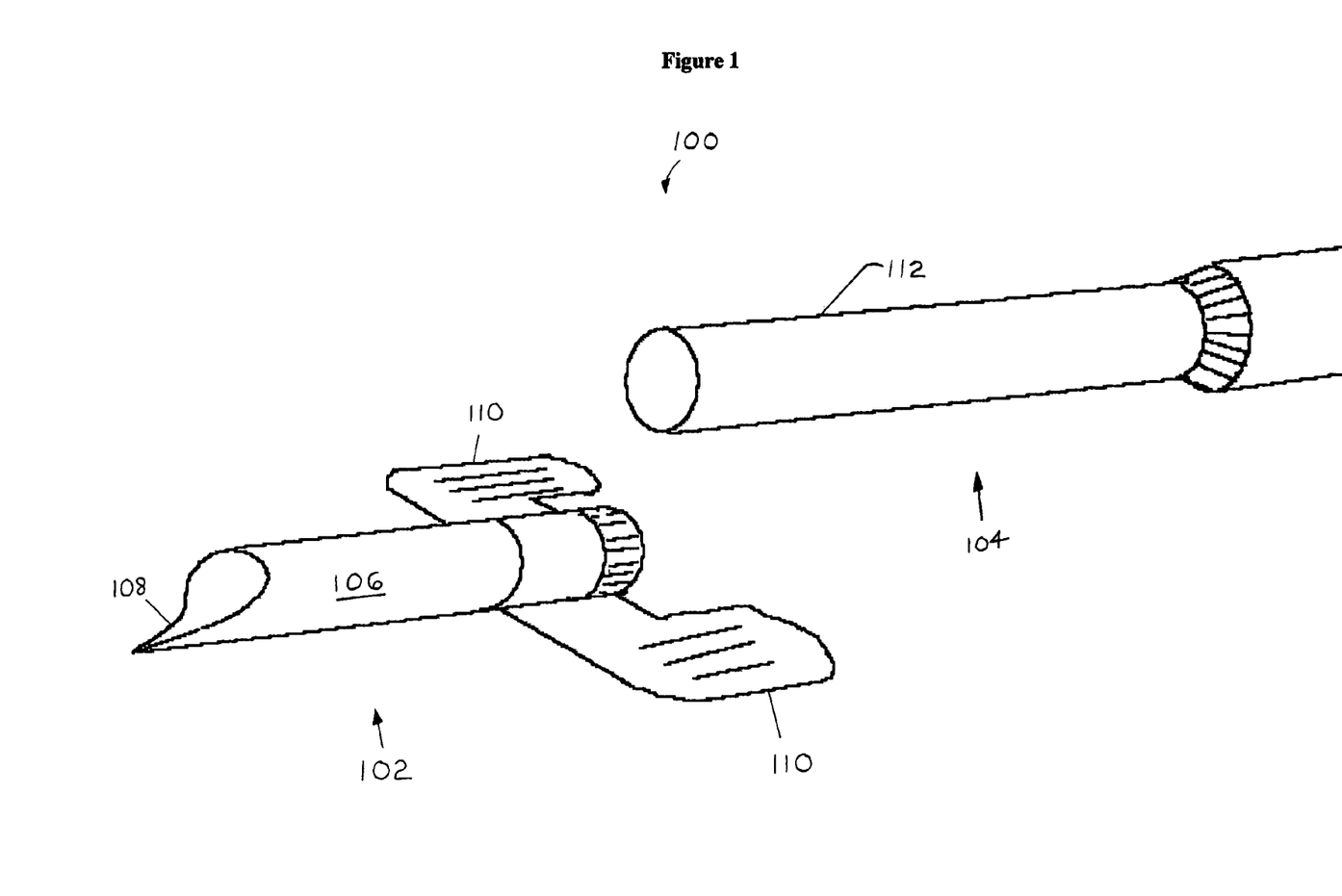
FIG. 1 depicts an exploded view of the Khan Access Preservation System. Specifically, it reveals numerous components of the system and their functional relation to one another.

The instant invention, as shown in FIG. 1, relates to a novel design for such an access.

Many times, patient access is needed for dialysis treatments as often as thrice weekly. There are two primary blood accesses: permanent and temporary. Permanent accesses are designed to stay in the body for longer periods of time. Temporary accesses are in the body for a short amount of time.

Overview of Current Modes of Access.

Two common types of permanent accesses are:
1. AV Graft
2. AV Fistula

The acronym "AV" refers to "arteriovenous," referring to the arteries and veins in the human body.

Figure 2:
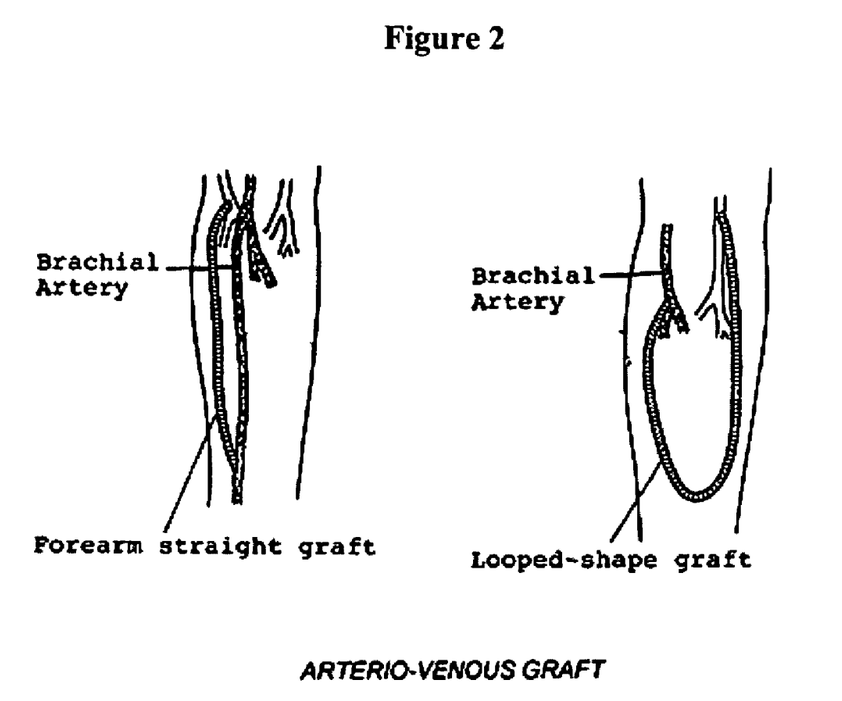
FIG. 2 depicts an illustration of an arterio-venous graft.

Referring, now, to FIG. 2, an AV graft construction is depicted. An AV graft connects an artery to a vein under the skin by means of an artificial blood vessel. These constructions are commonly used when the patient's own blood vessels are too small or weak for fistula construction (an alternative access mechanism discussed below). Often, these patients are elderly or have pre-existing diabetes mellitus.

AV grafts, which are most commonly placed in the upper arm, lower arm, and/or thigh, comprise a conduit which is either straight or U-shaped. The graft is placed close to the surface of the skin for easier needle insertion.

The graft may be made from a leg vein or cow (i.e., bovine) vein; it may also be made from a variety of artificial or synthetic (i.e., man-made) materials, such as polytetrafluoroethylene. Some synthetic constructions are known by their brand names (e.g., Gortex, Impra).

After the graft is placed, two to four weeks should pass before the graft is punctured to allow adequate healing and sufficient growth of tissue to stabilize the graft.

Figure 3:
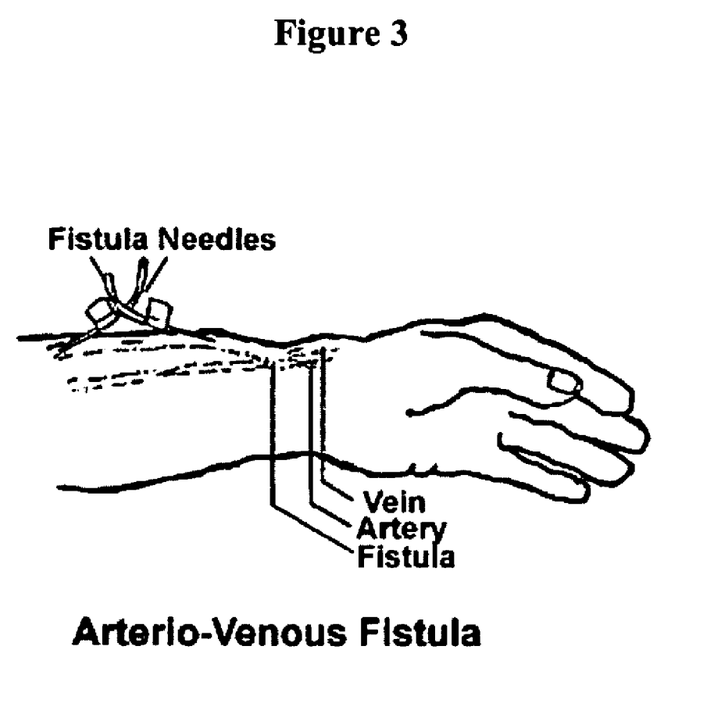
FIG. 3 depicts an illustration of an arterio-venous fistula.

Referring, now, to FIG. 3, an AV fistula is depicted. An AV fistula is a close connection made directly between an artery and vein. The artery and vein are joined together under the skin.

The AV fistula is created internally, and it is used for prolonged periods of time. Its construction involves a small operation to directly join an artery and vein, allowing arterial blood to flow directly into the vein. According to information presented during a symposium at the University of Cincinnati Medical Center (i.e., "Angio Access for Dialysis"), an AV fistula usually lasts longer and usually has fewer problems than does a synthetic graft (like Gortex).

Blood vessels of the arm are usually chosen (e.g., at the wrist or upper forearm). Due to arterial pressure, the vein will subsequently increase in size and its walls will thicken. Once the vein has had time to heal, it is easier to put a needle into the vein, so that the blood will flow through the dialyzer by means of the blood pump on the machine.

The amount of time after construction/placement before an access may be used depends upon the type of access. Fistula maturation generally requires three to four months (so that the vein has time to heal, enlarge, and support sufficient blood flow for use in hemodialysis).

The typical locations for hemodialysis access are:
1. Arm: Right or left, upper or lower; and
2. Leg: Right or left, upper or lower.

Problems Associated with Current Access Methods

Although the accesses just described are highly effective, and constitute a critical "life line" for the patient, they, like many other biological systems, are somewhat fragile, and both types of accesses feature potential dangers.

For example, accesses must be carefully managed because, typically, they are punctured (not uncommonly twice) for each treatment.

One of the most important things to do, therefore, is to rotate needle stick placement sites. Changing the stick sites for each dialysis treatment allows the body to have the time necessary for healing of those localized sites to occur. In the case of a routine cannulation, for example, healing occurs fairly rapidly, so site rotation is a convenient and effective method of ensuring healthy access sites; however, if a laceration and/or infiltration of the stick site has occurred, it can take as long as two to six weeks for healing of a stick site to occur.

Thus, in a nutshell, healing time is important. Like your skin, your artery-vein graft needs time to recover from repeated needle sticks. If the site is not rested, it will become weak, resulting in a weak region in the access called an aneurysm. Rotating needle stick sites helps keep an access strong.

Another important current practice involves access immobilization during treatment.

Many lay observers are surprised to learn that one of the greatest possible dangers to the integrity of a patient's access site is the possible laceration and/or infiltration of the AV graft or fistula by the sharp point of the needle. This type of damage can be serious; not uncommonly, it requires the patient to visit a vascular surgeon for repair or replacement.

As a consequence, the current state of the art in treatment recognizes that needles should be taped securely to keep them from moving and causing damage to the access during the dialysis. Thus, once the patient has been cannulated (i.e., punctured with the needle), the needle is then taped in place securely to help minimize movement. The patient is further instructed to remain as still as possible for the duration of the treatment.

Most patients do a fine job of remaining fairly immobile during treatment, but there are naturally times when an involuntary movement may cause the patient's access site to move. During movement, the potential for inadvertent damage is substantially increased. And this damage can occur at the beginning of the hemodialysis treatment (during insertion of the needle), during the treatment itself, or it can even occur after the completion of hemodialysis treatment (during the removal of the needle).

A Critical Need: a Safer Form of Access.

What is needed, in the field of hemodialysis treatments and, indeed, in any fluid/medication-delivery applications such as intravenous cannulation, is a way to utilize the sharp puncture point of the needle in order to gain access during cannulation but to simultaneously minimize the potential of the same sharp needle further puncturing the region after cannulation (i.e., during and at the close of treatment).

BRIEF SUMMARY OF THE INVENTION

An access device is disclosed that comprises two main assemblies. The first assembly is the cylindrical cannulation assembly. This is the needle-point-bearing assembly which facilitates cannulation (i.e., insertion of the assembly into the arm of the patient). The cylindrical cannulation assembly comprises a cannulation cylinder which has an insertion point (i.e., the needle puncture point) at a first end.

The second main assembly of the invention is the cylindrical conduit assembly. This is the assembly that facilitates fluid flow during treatment free of the worry that the very needle which facilitated access will internally lacerate the blood vessel. The cylindrical conduit assembly comprises a cylindrical conduit which is telescopically positioned within the cannulation cylinder.

The cannulation cylinder and cylindrical conduit longitudinally move relative to one another, and they are relatively placed at two effectual positions. In the first position (to be used before and during cannulation), the blunt end of the cylindrical conduit is positioned a rearward distance from the insertion point to facilitate cannulation. In the second position (to be used after cannulation), the blunt end of the cylindrical conduit is positioned substantially at or forward of the insertion point so as to protect the blood vessel from abrasion or puncture.

The access device can further be fitted with a locking device to secure the cylindrical conduit relative to the cannulation cylinder at either or both of the first and second positions.

BRIEF DESCRIPTION OF THE SEVERAL VIEWS OF THE DRAWINGS

FIG. 1 through FIG. 5 provide views of an initial embodiment (i.e., a first embodiment) of the Khan Access Preservation System.

FIG. 6 through FIG. 13 provide views of a refined embodiment (i.e., a second embodiment) of the Khan Access Preservation System.

DETAILED DESCRIPTION OF THE INVENTION

Referring again to the figures, and, specifically, to FIG. 1, an exploded view of the Khan Access Preservation System 100 is shown. This figure reveals numerous components of the system and their functional relation to one another.

The visible assemblies consist of (a) a hollow cylindrical puncture/insertion assembly 102; and (b) a blunt cylindrical steady flow access device 104. The puncture/insertion assembly is a hollow cylindrical tube 106 with a sharp beveled point 108 to facilitate cannulation of the patient's access. A key aspect of the design of the puncture/insertion assembly is that its shape should facilitate smooth insertion into the skin and entry into the patient's blood vessel. The puncture/insertion assembly also utilizes attached wings 110 that aid the patient or patient care member in cannulation (i.e., puncture point insertion) of the access site. The wings also provide stability when the whole system is taped to the patient's limb.

The blunt cylindrical steady flow access device 104 is also a cylindrical member; it is a blunt hollow cylinder 112 that, when properly moved forward into position, provides the much-needed (and presently missing) protection of the patient's access vessel.

Figure 4:
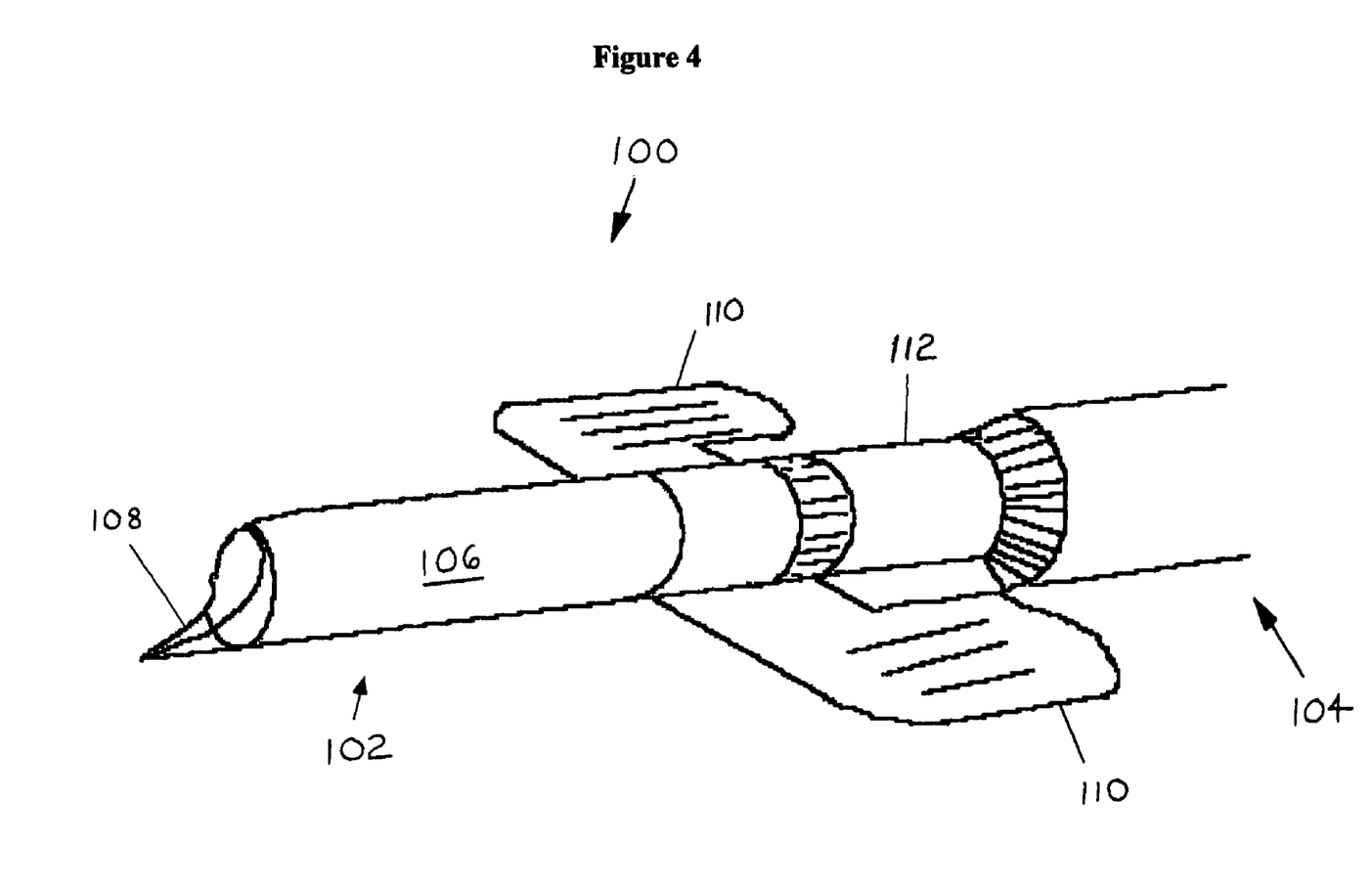
FIG. 4 depicts an illustration of the Khan Access Preservation System in the cannulation (i.e., puncture point insertion) position.

Referring, now, to FIG. 4, an illustration is provided depicting the Khan Access Preservation System in the cannulation (i.e., puncture point insertion) position. Note that the blunt cylindrical steady flow access assembly 104 does not protrude beyond the edge of the puncture/insertion assembly 102. This allows for smooth cannulation (i.e., puncture point insertion) of the patient's access vessel.

Figure 5:
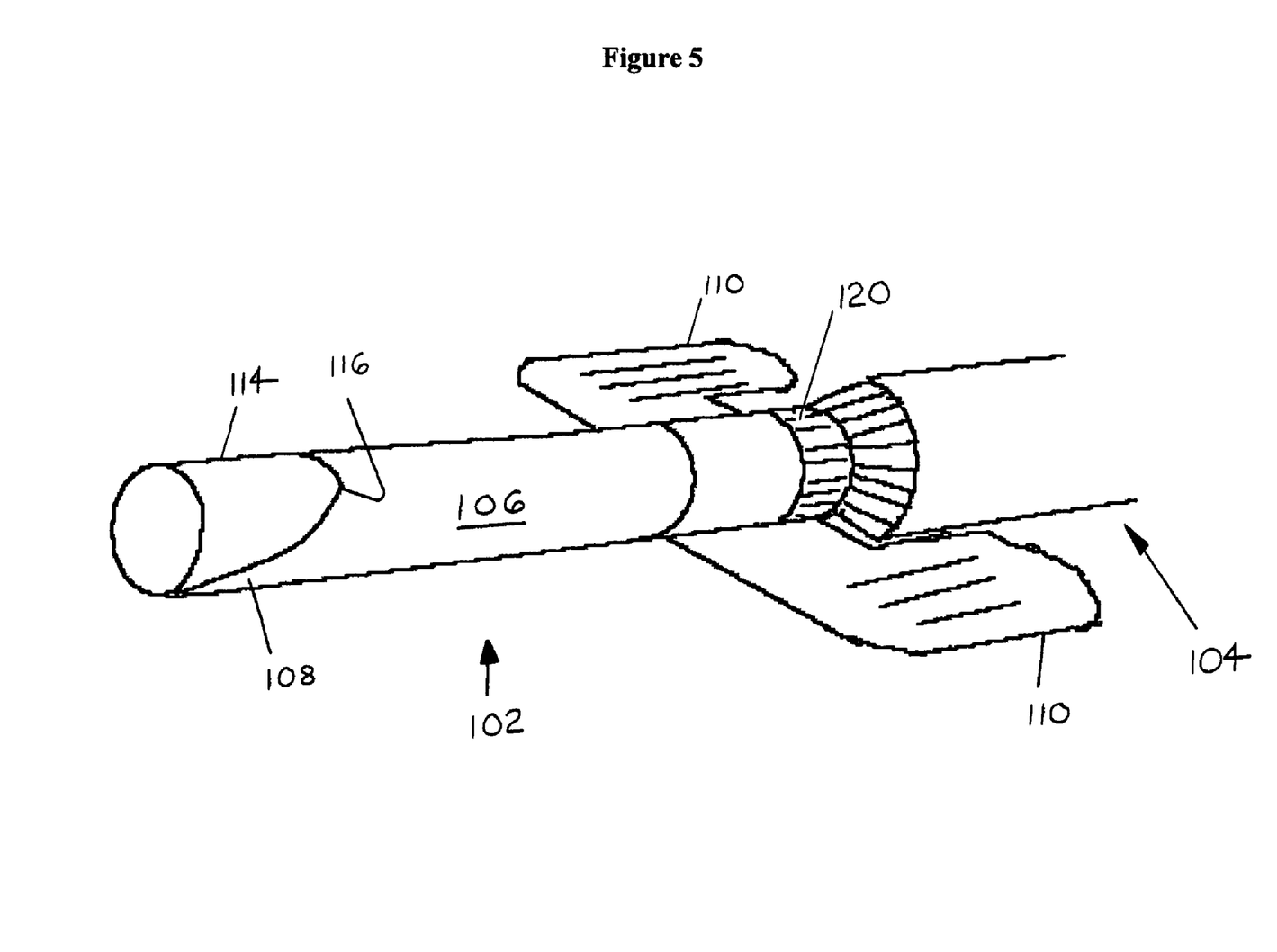
FIG. 5 depicts the Khan Access Preservation System in the treatment (or steady-state or 'run') position.

Referring to FIG. 5, the Khan Access Preservation System 100 is depicted in the operating (or steady-state or 'run') position. Note that the puncture/insertion assembly 102 has been retracted a predetermined length (relative to the blunt cylindrical steady flow access assembly 104) to ensure that the sharp point 108 of the needle is now safely protected behind the blunt end 114 of (and in close proximity to the wall of) the cylindrical steady flow access assembly 104. Furthermore, it is desirable for the puncture/insertion assembly 102 to be locked into position (again, relative to the blunt cylindrical steady flow access assembly 104) so that the sharp point 108 of the needle remains in a secure, safe position during treatment.

It will be apparent to the reader that the two annular assemblies must feature a narrow annulus 116 (i.e., be telescoped in close proximity) to prevent leakage. It will also be apparent that an important overall design objective is to: (a) minimize the outside diameter (OD) of the hollow cylindrical tube 106 (to maximize patient comfort and minimize shock to the patient's arteries and veins), while (b) maximizing the inner diameter (ID) of blunt hollow cylinder 112 (to maximize the flow rate of blood), while (c) minimizing the annulus 116 as much as practicable so as to maximize the ID of blunt hollow cylinder 112 (to maximize the flow rate of blood) and prevent leakage while simultaneously avoiding interference and/or frictional effects problems associated with the sliding engagement of hollow cylindrical tube 106 and blunt hollow cylinder 112.

Furthermore, it will also be apparent to the astute reader that the key concept upon which the invention is based is the relative movement of the puncture/insertion assembly 102 vis-à-vis the cylindrical steady flow access assembly 104. Thus, whether the assembly operates via retraction of the puncture/insertion assembly 102 (relative to the cylindrical steady flow access assembly 104) or projection/insertion of the cylindrical steady flow access assembly 104 (relative to the puncture/insertion assembly 102) is, in the main, immaterial to the primary benefit imparted by the invention: protection of the patient's blood vessels from unnecessary lacerations.

A variety of locking mechanisms 120 will become apparent to the person of ordinary skill in the art. However, the desired mechanism will effectually and cost-effectively address the demands of the patient environment in which the invention is used. Generally speaking, it is desirable for the invention to facilitate effective cannulation and patient treatment.

Towards that end, a locking mechanism would, at a minimum, secure the relative position of the puncture/insertion assembly 102 vis-à-vis the blunt cylindrical steady flow access assembly 104 during treatment (to protect the vessel). In addition, such a locking mechanism might also secure the relative position of the puncture/insertion assembly 102 vis-à-vis the blunt cylindrical steady flow access assembly 104 before treatment during cannulation (to facilitate cannulation without obstruction by the blunt cylindrical steady flow access assembly 104).

A Refined Embodiment

Figure 6:
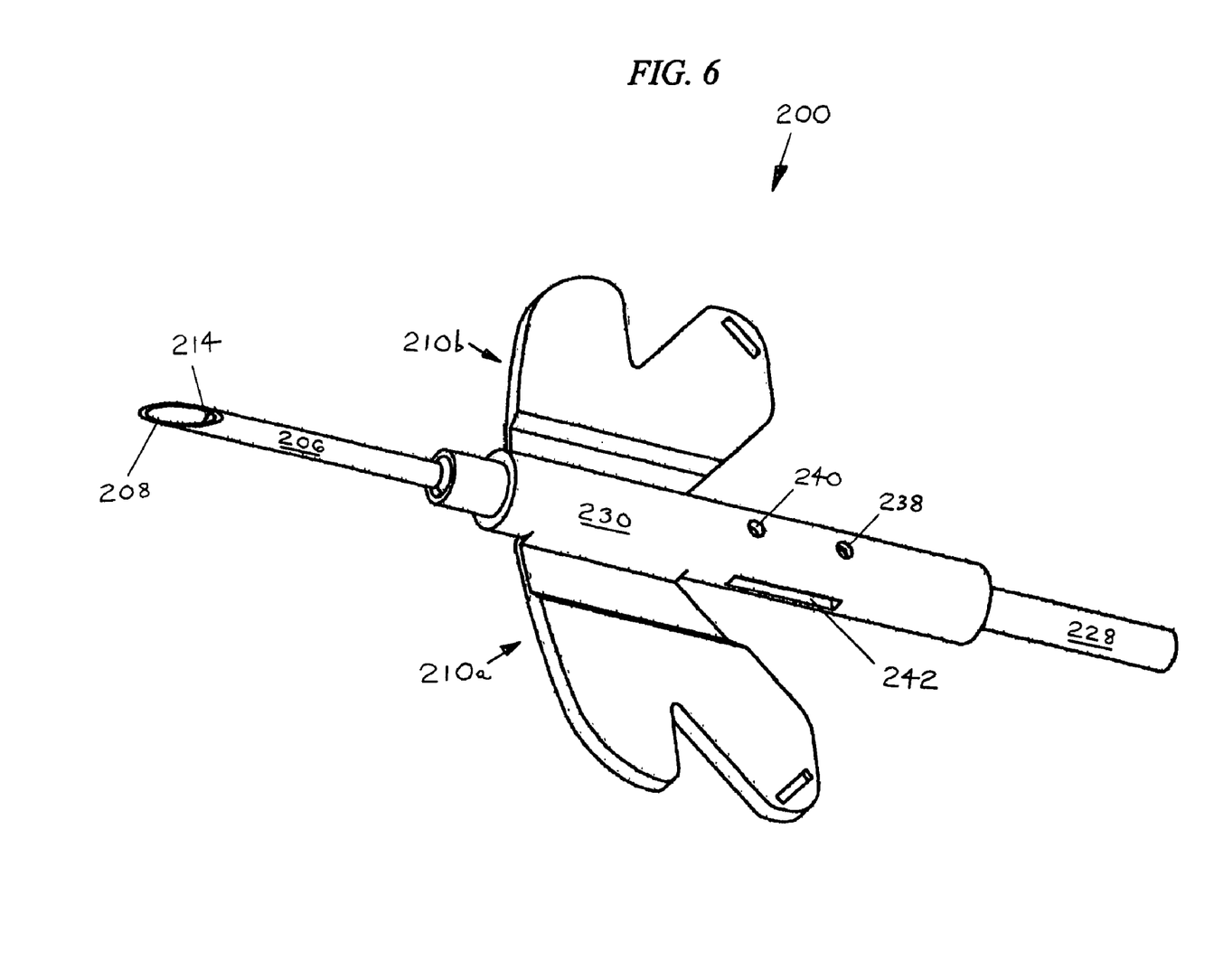
FIG. 6 provides a perspective view of a second embodiment of the Khan Access Preservation System in the cannulation (or insertion) configuration.
Figure 7:
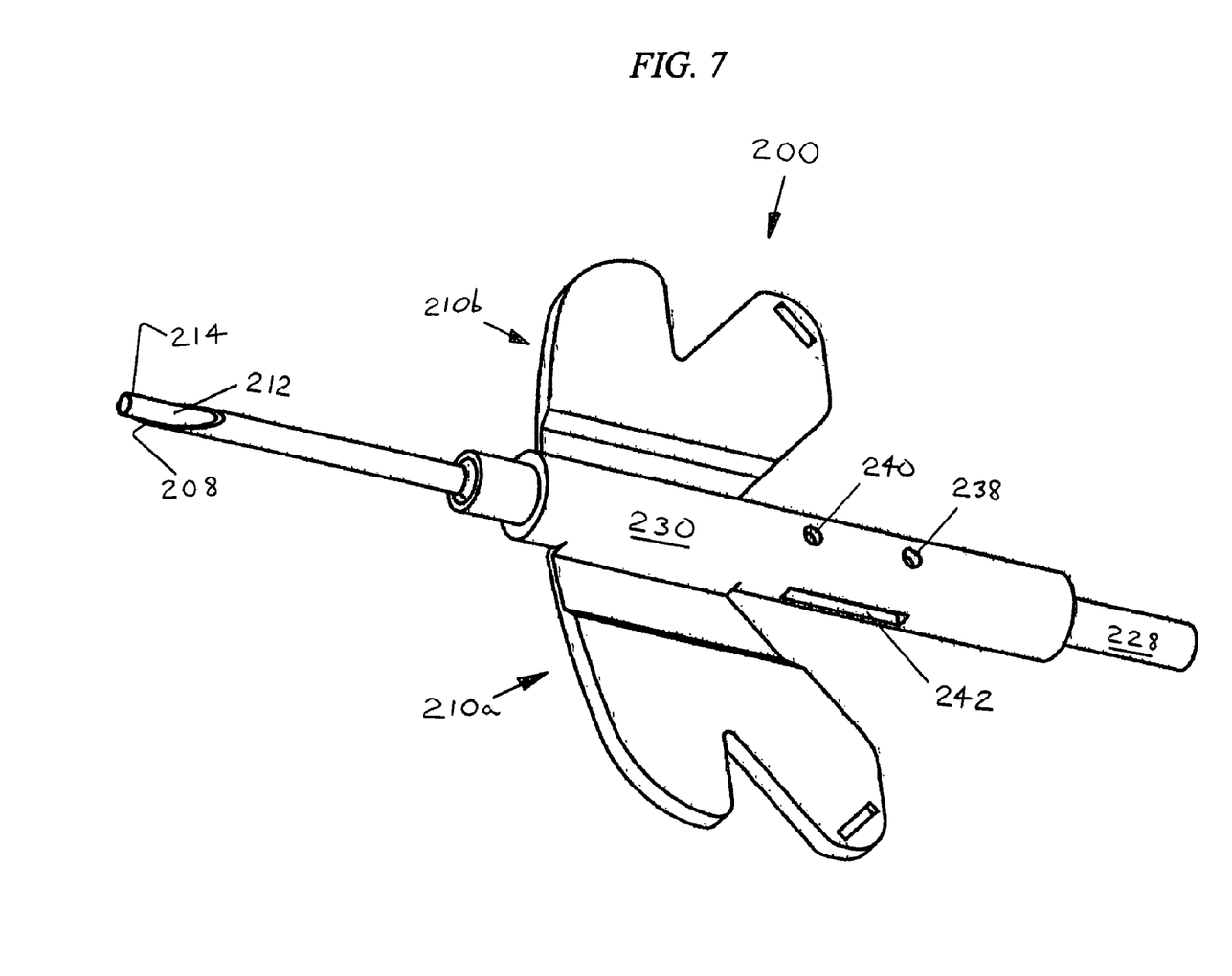
FIG. 7 provides a perspective view of a second embodiment of the Khan Access Preservation System in the steady-state (or steady flow or operating or operation) configuration/mode of operation.

Turning, now, to FIG. 6 and FIG. 7, perspective views of a refined embodiment 200 (i.e., a second embodiment 200) of the Khan Access Preservation System are shown. These figures reveal the overall configuration of the system in the cannulation position (see FIG. 6) and the steady state operation or 'run' position (see FIG. 7).

Figure 8:
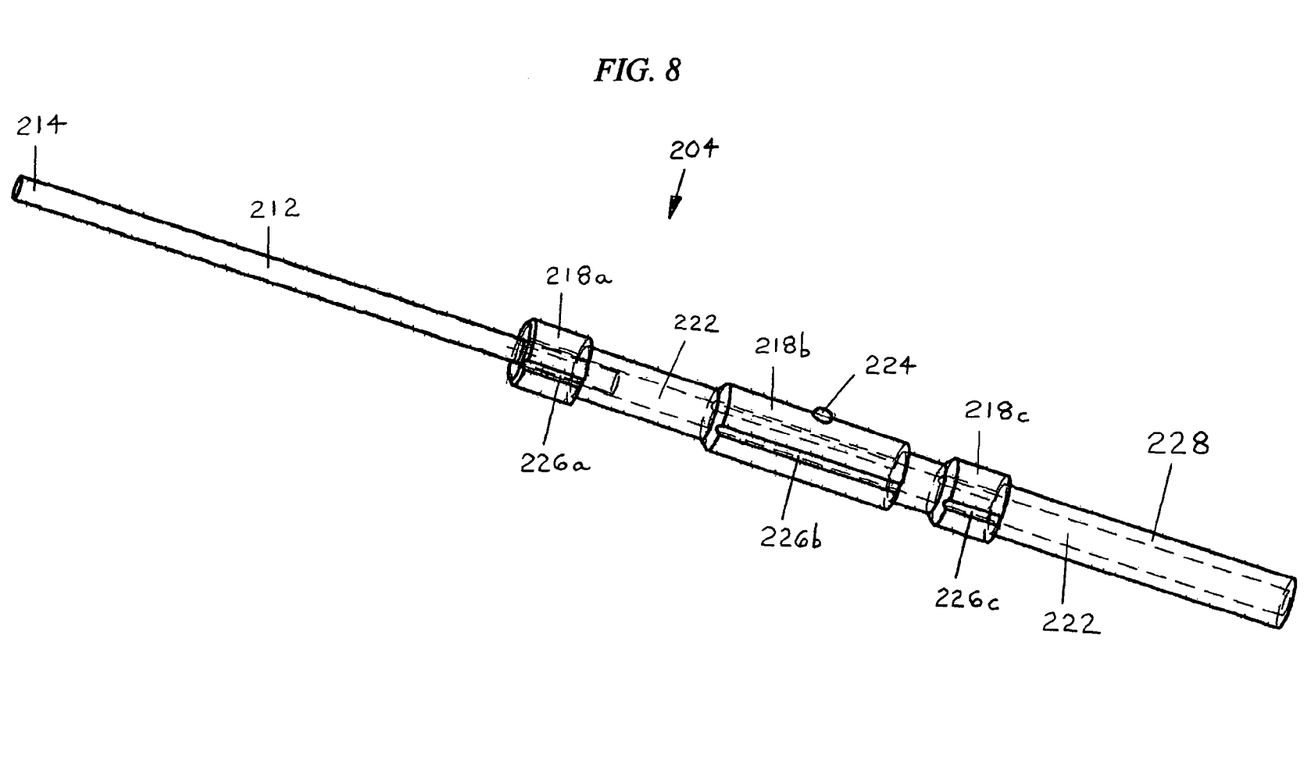
FIG. 8 provides a detailed perspective view of the steady flow access assembly.
Figure 9:
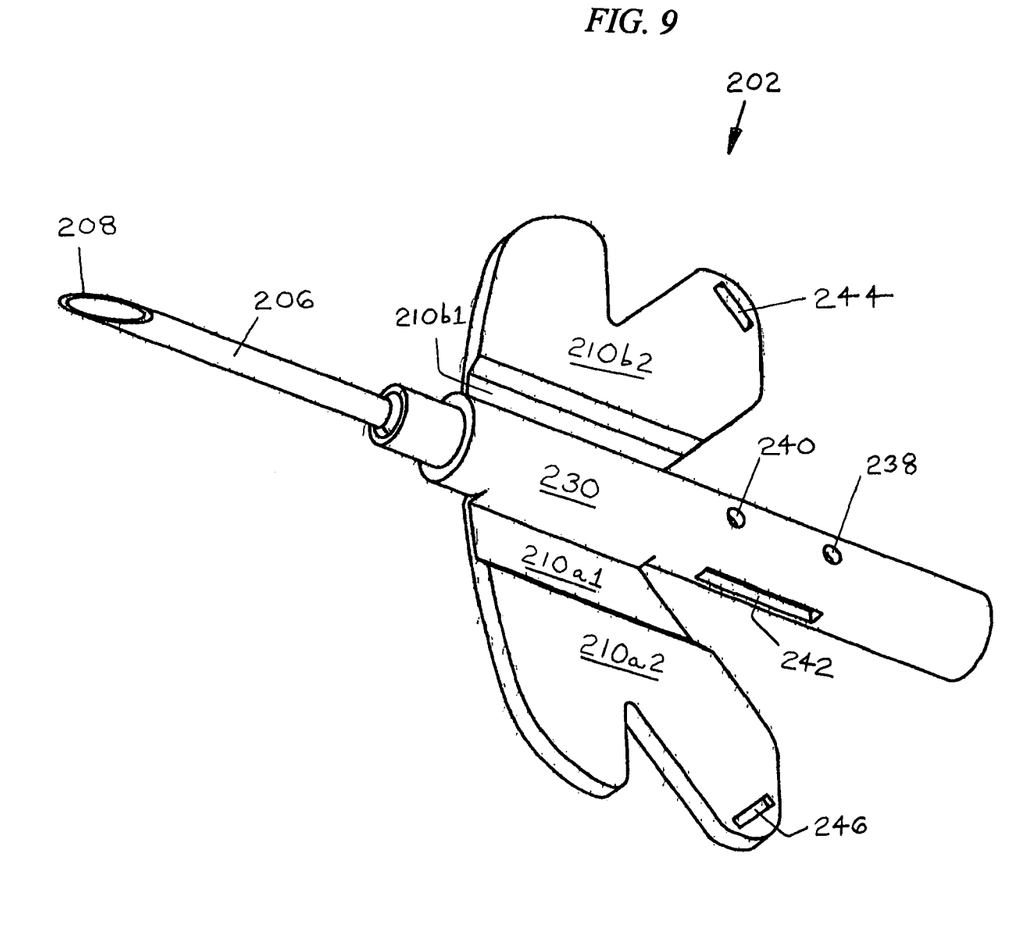
FIG. 9 provides a detailed perspective view of the puncture/insertion assembly.

Notice, in FIG. 6, that the steady flow access assembly 204 (an internal assembly shown in detail in isolation in FIG. 8) does not protrude beyond the edge of the puncture/insertion assembly 202 (an external assembly shown in detail in isolation in FIG. 9). In particular, notice the position of the insertion assembly point 208 relative to the steady flow access assembly cylinder blunt end 214. This allows for smooth cannulation (i.e., puncture point insertion) of the patient's access vessel.

Referring to FIG. 7, the Khan Access Preservation System 200 is depicted in the treatment (or steady-state or 'run') position. Note that the puncture/insertion assembly 202 has been retracted a predetermined length (relative to the steady flow access assembly 204) to ensure that the insertion assembly point 208 of the needle is now safely protected behind the steady flow access device cylinder blunt end 214 of (and in close proximity to the wall of) the steady flow access assembly cylinder 212.

In both FIG. 6 and FIG. 7, it is desirable for the positions of the puncture/insertion assembly 202 and the steady flow access assembly 204 to be locked relative to one another, so that, both during cannulation and afterwards, these two assemblies do not move relative to one another. The locking mechanism 220 which accomplishes this (which is defined in terms of the interaction of certain portions of the puncture/insertion assembly 202 and the steady flow access assembly 204 and which is not separately designated in FIG. 6 and FIG. 7) will be described hereinbelow.

Figure 10:
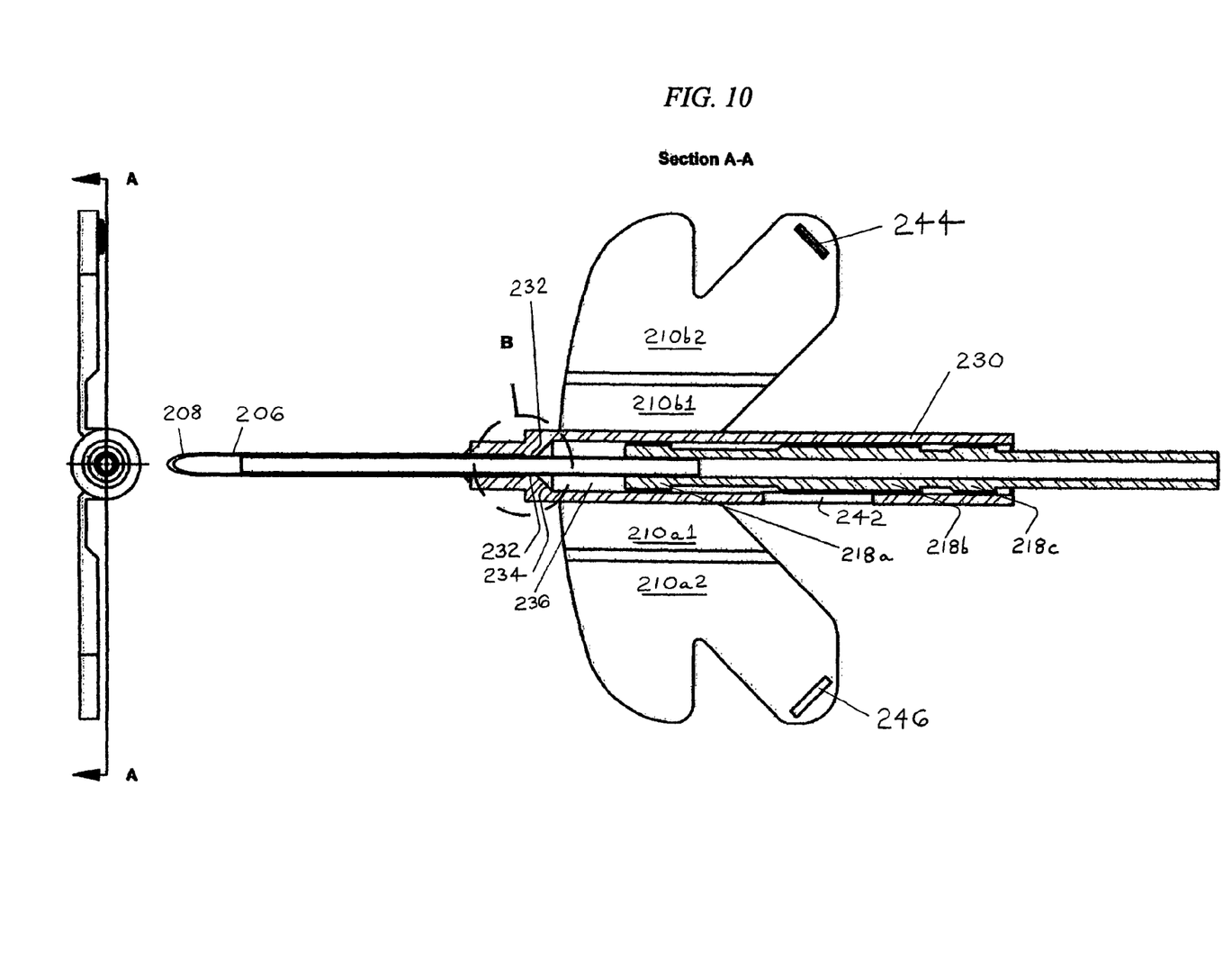
FIG. 10 provides a cross-sectional view of the assembled refined embodiment (i.e., the second embodiment) of the Khan Access Preservation System.

Before reviewing each of them in detail, it is helpful to perform a cursory comparative review of FIG. 8, FIG. 9, and FIG. 10. The comparison reveals that, as in the first embodiment, in this rather elegant design, there are two main assemblies: (a) the puncture/insertion assembly 202 shown in detail in isolation in FIG. 9; and (b) the steady flow access assembly 204 shown in detail in isolation in FIG. 8. A cursory review of FIG. 10 reveals how several of the operative components of the steady flow access assembly 204 are contained within (and are in a sliding engagement with) several components of the puncture/insertion assembly 202, the details of which will be explained further hereinbelow.

Turning, now, to FIG. 8 specifically, a detailed perspective view of the steady flow access assembly 204 is shown.

As in the case of the first embodiment, the steady flow access assembly 204 comprises a steady flow access assembly cylinder 212 which provides a conduit for the passage of blood during steady state operation of the invention 200. The steady flow access assembly cylinder 212 is longitudinally moved and rotated by the user within the invention 200 by means of various actuator portions to be now described.

In general, the user of the invention 200 moves the steady flow access assembly cylinder 212 forward and backward (in a sliding movement relative to the puncture/insertion assembly 202) by grasping and operating the access assembly actuator/gripping sleeve 228 (actually, in many embodiments, a blood transport tube (not shown) will have been slipped over access assembly actuator/gripping sleeve 228 (in a tight frictional fit and perhaps even fastened or glued into place) so that, when the user operates the access assembly actuator/gripping sleeve 228, he/she actually does so by grasping and operating the portion of the blood transport tube overlapping the access assembly actuator/gripping sleeve 228). As will be explained further hereinbelow, it is also possible to rotate the steady flow access assembly cylinder 212 clockwise and counterclockwise (again relative to the puncture/insertion assembly 202) by similarly operating the access assembly gripping sleeve 228.

The outside diameter of the actuator/gripping sleeve 228 is obviously greater than that of the steady flow access assembly cylinder 212 and yet it is also less than the inner diameter of the insertion assembly actuator/gripping sleeve 230 within which it operably resides.

To align both the steady flow access assembly cylinder 212 and the actuator/gripping sleeve 228, while simultaneously managing frictional effects, one or more alignment sleeve sections 218a, 218b, 218c are utilized. As best seen in FIG. 10, the outer diameter of these alignment sleeve sections 218 is designed to closely fit within the inner diameter of the insertion assembly actuator/gripping sleeve 230 so as to effectuate alignment of the steady flow access assembly cylinder 212 and the actuator/gripping sleeve 228 while simultaneously allowing for smooth and easy longitudinal sliding movement or rotation of the steady flow access assembly 204.

Returning, now, to FIG. 8, notice that the actuator/gripping sleeve 228, like the steady flow access assembly cylinder 212, is a cylindrical member, and its hollow interior, in communicative conjunction with the hollow interior of the steady flow access assembly cylinder 212, defines a single, integrated steady flow access assembly passageway 222 for the passage of blood. In fact, whether the steady flow access assembly cylinder 212 and the actuator/gripping sleeve 228 are separate components in fluid communication (as shown) or are fashioned as a single unitary material body is immaterial to the operability of the invention 200.

Notice the alignment sleeve section vents 226a, 226b, 226c. These alignment sleeve section vents 226 help to ensure that, as the forwardmost alignment sleeve section 218a is translated forward, air is not trapped and compressed within the cavity 236; rather, the air contained within cavity 236 easily and conveniently vents as the steady flow access assembly 204 is translated forward thus ensuring minimal resistance to forward translation.

Finally, note the presence of a locking dimple 224. The operation of the locking dimple 224 is outlined more fully hereinbelow. Suffice it to say at the moment that it facilitates locking the relative position of the steady flow access assembly 204 vis-à-vis the puncture/insertion assembly 202 in one of two operative locations: (a) the cannulation position (i.e., the desired invention configuration during which insertion of the insertion assembly point 208 into the arm of the patient occurs); and (b) the steady state operation position (i.e., the desired safe invention configuration during which hemodialysis occurs).

Turning, now, to FIG. 9, a detailed perspective view of the puncture/insertion assembly 202 is shown.

The insertion assembly 202 comprises a cylindrical insertion assembly tube 206 featuring a hollow interior and a sharp beveled insertion assembly point 208 to facilitate cannulation of the patient's access. A key aspect of the design of the puncture/insertion assembly is that its shape should facilitate smooth insertion of the insertion assembly point 208 into the skin and entry into the patient's blood vessel.

Notice that the puncture/insertion assembly 202 also features an insertion assembly actuator/gripping sleeve 230. The insertion assembly actuator/gripping sleeve 230 makes handling of the invention generally, and the cannulation and steady state operation of the invention 200, much easier.

Notice as well that the puncture/insertion assembly 202 also utilizes attached insertion assembly wings 210a, 210b which aid the patient caregiver in effectuating cannulation (i.e., puncture point insertion) of the access site. A close examination of each of the insertion assembly wings 210a, 210b reveals that each wing features sections of varying thickness. For example, a close examination of FIG. 9 reveals that insertion assembly wing 210a features an outer, radially distant portion of the wing 210a2 which is much thicker than the inner, radially proximate portion of the wing 210a1. The variance in the thickness makes it easier for the caregiver to fold the insertion assembly wings 210a, 210b upward if he or she desires, so as to utilize the wings in further grasping and utilizing the invention 200 to effectuate cannulation. An optional insertion assembly wing dimple 244 is shown on insertion assembly wing 210b and is designed to drop into place with its mate, the insertion assembly wing hole 246 appearing on insertion assembly wing 210a, so as to facilitate handling the invention 200 when the insertion assembly wings 210a, 210b are folded/wrapped into an upwards position during cannulation.

The insertion assembly wings 210a, 210b also provide stability when, during steady state operation, the invention 200 is taped to the patient's limb.

Notice the cannulation locking hole 238, the steady state locking hole 240, and the translation slot 242. These components, in conjunction with the locking dimple 224 (as shown in FIG. 8 and discussed hereinabove), cooperate to provide a locking mechanism which secures the position of the steady flow access assembly 204 (relative to the puncture/insertion assembly 202) in one of two operative locations: (a) the cannulation position (i.e., the desired invention configuration during which insertion of the insertion assembly point 208 into the arm of the patient occurs); and (b) the steady state operation position (i.e., the desired safe invention configuration during hemodialysis).

During cannulation, the steady flow access assembly 204 is in a rearward location relative to the puncture/insertion assembly, and the locking dimple 224 is firmly positioned within cannulation locking hole 238. This relative positioning of the invention 200 assemblies is shown in detail in FIG. 13.

Returning, now to FIG. 9, it should be noted that, after cannulation has occurred, and the invention 200 is to be operated in a steady-state mode of operation which minimizes the potential for laceration of the vein upon inadvertent movement of the patient's limb or the invention 200 itself, the user/caregiver grasps the insertion assembly actuator/gripping sleeve 230 to steady the invention 200, and he or she rotates the access assembly actuator/gripping sleeve 228 (again, as described above, likely namely that portion of the access assembly actuator/gripping sleeve 228 which is overlapped by the blood transport tube (not shown) which the user effectually grasps) in a counterclockwise rotation (viewing the device down its longest axis from the access assembly actuator/gripping sleeve 228 to the insertion assembly point 208) against modest resistance so that locking dimple 224 exits cannulation locking hole 238 and enters translation slot 242. Then, the user translates the steady flow access assembly 204 forward relative to the puncture/insertion assembly 202 (against minimal resistance owing to the translation slot 242) until the locking dimple 224 reaches the forwardmost position within the translation slot 242, at which time the user rotates the access assembly actuator/gripping sleeve 228 clockwise so as to bring the locking dimple 224 into the steady state locking hole 240, locking the configuration of the invention 200 into a safe, steady-state mode of operation for the duration of the treatment. This relative positioning of the invention 200 assemblies, which provides the much-needed and presently missing protection of the patient's access vessel (and which even provides an additional level of protection to the caregiver against accidental needle pricks upon removal of the device from the patient), is shown in detail in FIG. 12.

It should also be noted that an alternative locking mechanism, not shown in the figures, could be utilized that features a translation slot 242 which is between (and in line with) the cannulation locking hole 238 and steady state locking hole 240. In this embodiment of the locking mechanism, the locking dimple 224 is never rotated counterclockwise or clockwise; rather, after cannulation, it is simply translated from the cannulation locking hole 238 to steady state locking hole 240. Locking of the locking dimple 224 in place during cannulation is effectuated by means of a first translation slot bottleneck portion (or cannulation translation slot bottleneck portion). This first translation slot bottleneck portion is simply a very short longitudinal segment of the translation slot 242 (located very close to the cannulation locking hole 238) which is somewhat narrower than that of the remainder of the translation slot 242. This short bottleneck portion holds the locking dimple 224 in place during cannulation.

After cannulation, in regards to this alternative locking mechanism, the locking dimple 224 is urged forward, overcoming the modest resistance imparted by the first translation slot bottleneck portion, so that it slides easily along the translation slot 242 until it encounters a second translation slot bottleneck portion (or steady state translation slot bottleneck portion). This second translation slot bottleneck portion is simply a very short longitudinal segment of the translation slot 242 which is also somewhat narrower than that of the remainder of the translation slot 242. Importantly, it is located very close to the steady state locking hole 240. After the locking dimple 224 has traveled essentially the entire effective length of the translation slot 242, it encounters the second translation slot bottleneck portion; the user continues to urge the locking dimple 224 forward so that it overcomes the modest resistance imparted by the second translation slot bottleneck portion, snapping gently into place within the steady state locking hole 240.

Turning, now, to FIG. 10, a cross-sectional view of the assembled invention 200 is shown. The invention 200 is clearly in the cannulation configuration as evidenced by the rearward position of the steady flow access assembly cylinder blunt end 214 relative to the insertion assembly point 208.

Figure 11:
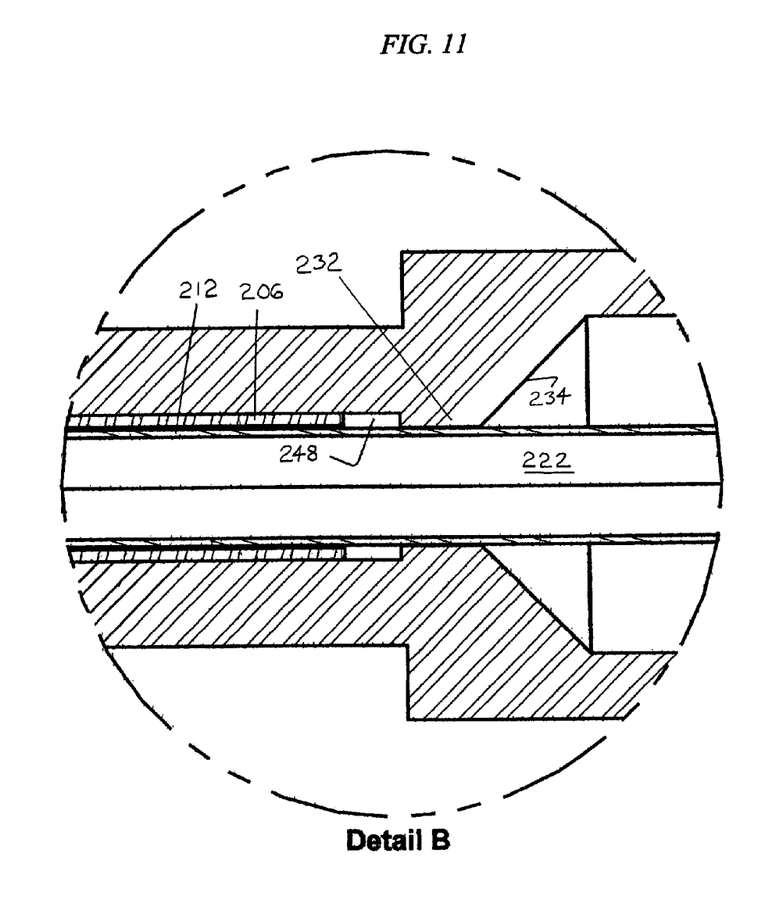
FIG. 11 depicts a close-up cross-sectional view of a portion of the second embodiment shown in FIG. 10.

FIG. 11 depicts a close-up cross-sectional view of a portion of the invention shown in FIG. 10. This drawing clarifies the design of the insertion assembly main seal 232. Although the annulus 216 defined between the interior wall of the insertion assembly tube 206 and the exterior wall of the steady flow access assembly cylinder 212 is a narrow one (i.e., one telescoped in close proximity) so as to maximize the effective flow rate of blood, minimize impact and discomfort to the patient, and avoid interference and/or frictional effects and leakage (as referenced hereinabove), additional leakage protection is provided by the insertion assembly main seal 232 which, by design, is in close frictional engagement with the steady flow access assembly cylinder 212.

The attentive reader will observe as well the frusto-conical or funnel-shaped rear face 234 of the insertion assembly main seal 232 which acts as a guide, facilitating the insertion of the steady flow access assembly cylinder 212 when the invention 200 is first assembled. In addition, a forward seal cavity 248 is defined between the forward face of the insertion assembly main seal 232 and the rearward face of the insertion assembly tube 206. This forward seal cavity 248 minimizes the likelihood of a shearing of any minute amounts of seal material near the forward face of the insertion assembly main seal 232 when the steady flow access assembly cylinder 212 is first introduced into the puncture/insertion assembly 202 during initial assembly of the invention 200.

Figure 12:
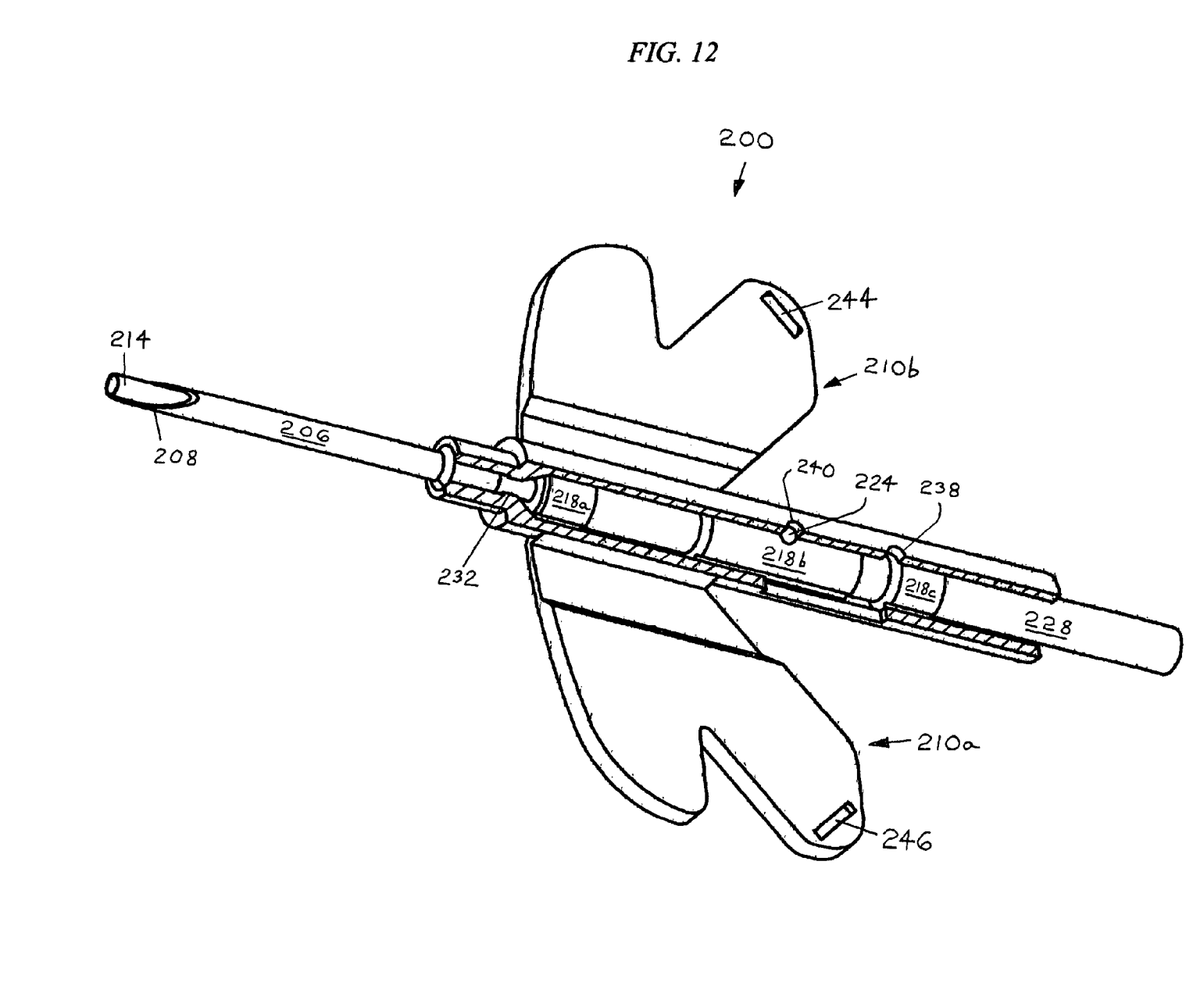
FIG. 12 provides a perspective view of the assembled refined embodiment (i.e., the second embodiment) of the Khan Access Preservation System in its steady-state mode of operation.

FIG. 12 provides a perspective view of the invention 200 in its steady-state mode of operation. In this configuration, the invention 200 provides a safe and superior mode of operation (providing a much-needed (and presently missing) protection of the patient's access vessel) for the duration of the hemodialysis treatment.

Figure 13:
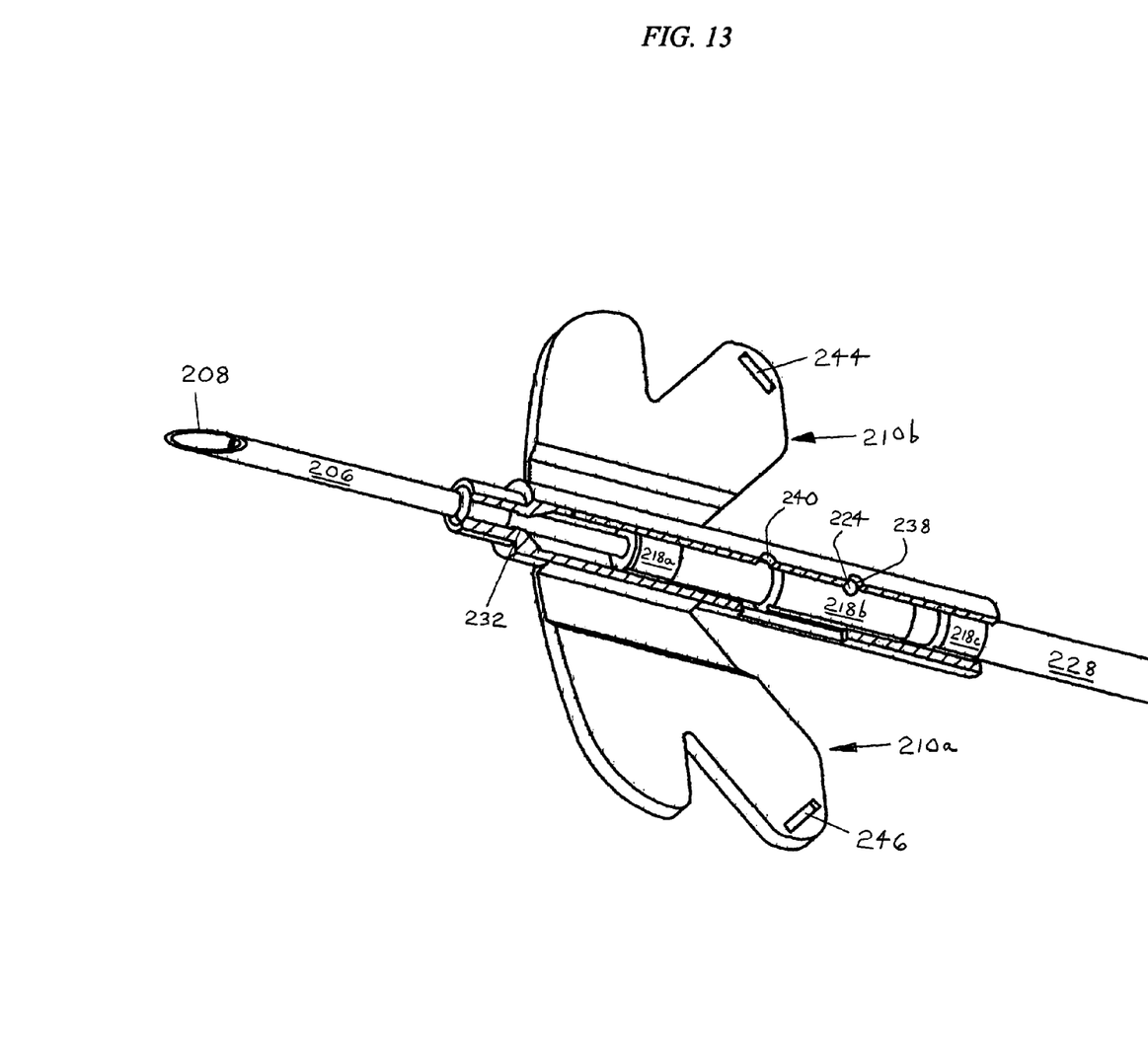
FIG. 13 provides a perspective view of the assembled refined embodiment (i.e., the second embodiment) of the Khan Access Preservation System in its cannulation mode of operation.

FIG. 13 provides a perspective view of the invention 200 in its cannulation mode of operation. This is perhaps most clearly evidenced by the rearward location of the steady flow access assembly 204 relative to the puncture/insertion assembly 202.

Finally, the subject of the best materials to use for the construction of the device is likely best left to the person of ordinary skill in the art. However, it is the inventors' belief, based upon the technical development work done to date, that the needle-type components (i.e., the insertion assembly tube 106, 206 and the steady flow access device cylinder 112, 212) should probably desirably be manufactured of three hundred four or three hundred sixteen medical grade stainless steel or the like (and/or possibly a high-performance plastic or reinforced composite material). The remaining parts of the puncture/insertion assembly 102, 202 should probably be made of a medical grade polypropylene, other high-performance plastic, or like material (possibly with a softening agent to enhance seal performance and provide a good tactile sensation at the locking mechanism), while the remaining parts of the steady flow access assembly 104, 204 should probably be made of a medical grade polycarbonate or medical grade acrylic, other high-performance plastic, or like material.

Although the invention has been described with reference to one or more preferred embodiments, this description is not meant to be construed in a limiting sense. Rather, various modifications of the disclosed invention, as well as alternative embodiments of the invention, will become apparent to persons of ordinary skill in the art, and these modifications, improvements, and alternative embodiments are intended to be encompassed within the metes and bounds of the patented invention as described in the following claims.

We claim:

1. An access device comprising:
   (a) a cylindrical cannulation assembly, said cylindrical cannulation assembly comprising a cannulation cylinder comprising an insertion point at a first end;
   (b) a cylindrical conduit assembly, said cylindrical conduit assembly comprising a cylindrical conduit and at least one alignment sleeve section to facilitate alignment of said cylindrical conduit within said cannulation cylinder and the easy sliding engagement of said cylindrical conduit within said cannulation cylinder, wherein at least one of said at least one alignment sleeve sections comprises an alignment sleeve section vent to vent air trapped in enclosed spaces between said cylindrical conduit assembly and cylindrical cannulation assembly, said cylindrical conduit telescopically positioned within said cannulation cylinder such that,
      (1) at a first position (to be used before and during cannulation), a first end of said cylindrical conduit, said first end being a substantially smooth right circular cylinder, is positioned a rearward distance from said insertion point to facilitate cannulation, and,
      (2) at a second position (to be used after cannulation), said first end of said cylindrical conduit is positioned within said cannulation cylinder substantially at or forward of said insertion point; and
   (c) a locking mechanism to secure the position of said cylindrical conduit relative to said cannulation cylinder at either said first position or said second position.

2. The access device of claim 1 wherein said cylindrical conduit is fitted with a conduit gripping sleeve to facilitate the longitudinal sliding movement of said cylindrical conduit within said cannulation cylinder.

3. The access device of claim 1 wherein said locking mechanism comprises a dimple on at least one of said at least one alignment sleeve sections, and an axially aligned cannulation locking hole, axially aligned steady state locking hole, and axially aligned but rotationally displaced translation slot on an insertion assembly gripping sleeve fitted to said cannulation cylinder, such that, at said first position, said dimple is positioned within said cannulation locking hole, and, at said second position, said dimple is positioned within said steady state locking hole.

4. The access device of claim 1 wherein said locking mechanism comprises a dimple on at least one of said at least one alignment sleeve sections, and an axially aligned cannulation locking hole, steady state locking hole, and translation slot on an insertion assembly gripping sleeve fitted to said cannulation cylinder, such that, at said first position, said dimple is positioned within said cannulation locking hole, and, at said second position, said dimple is positioned within said steady state locking hole.

5. The access device of claim 1 wherein said locking mechanism comprises a dimple on at least one of said at least one alignment sleeve sections and an axially aligned translation slot on an insertion assembly gripping sleeve fitted to said cannulation cylinder, such that, at said first position, said dimple is positioned at one substantial extremity of said translation slot, and, at said second position, said dimple is positioned at the opposite substantial extremity of said translation slot.

6. The access device of claim 1 wherein said cylindrical cannulation assembly comprises an insertion assembly gripping sleeve to facilitate the longitudinal sliding movement of said cylindrical conduit within said cannulation cylinder.

7. The access device of claim 1 wherein said cylindrical cannulation assembly comprises a cylindrical seal in tight engagement with the outer surface of said cylindrical conduit and in close proximity with the end opposite said first end of said cannulation cylinder so as to prevent continuous fluid communication through the annulus defined between the outer surface of said cylindrical conduit and the inner surface defined of said cannulation cylinder.

8. The access device of claim 7 wherein the rearward face of said cylindrical seal is a frusto-conical surface which facilitates the funneling insertion of said cylindrical conduit within said cannulation cylinder during manufacture of said access device.

9. The access device of claim 7 wherein the longitudinal displacement between the rearward face of said end opposite said first end of said cannulation cylinder and of said cylindrical seal defines a seal cavity which reduces shearing at access device assembly of the material of which said cylindrical seal is made.

10. An access device comprising:
(a) a cylindrical cannulation assembly, said cylindrical cannulation assembly comprising a cannulation cylinder comprising an insertion point at a first end;
(b) a cylindrical conduit assembly, said cylindrical conduit assembly comprising a cylindrical conduit fitted with at least one alignment sleeve section to facilitate alignment of said cylindrical conduit within said cannulation cylinder and the easy sliding engagement of said cylindrical conduit within said cannulation cylinder, said cylindrical conduit telescopically positioned within said cannulation cylinder such that,
   (1) at a first position (to be used before and during cannulation), a first end of said cylindrical conduit, said first end being a substantially smooth right circular cylinder, is positioned a rearward distance from said insertion point to facilitate cannulation, and,
   (2) at a second position (to be used after cannulation), said first end of said cylindrical conduit is positioned within said cannulation cylinder substantially at or forward of said insertion point; and
(c) a locking mechanism to secure the position of said cylindrical conduit relative to said cannulation cylinder at either said first position or said second position, said locking mechanism comprising a dimple on at least one of said at least one alignment sleeve sections, and an axially aligned cannulation locking hole, axially aligned steady state locking hole, and an axially aligned but rotationally displaced translation slot on an insertion assembly gripping sleeve fitted to said cannulation cylinder, such that, at said first position, said dimple is positioned within said cannulation locking hole, and, at said second position, said dimple is positioned within said steady state locking hole wherein
(d) said cylindrical cannulation assembly comprises a cylindrical seal in tight engagement with the outer surface of said cylindrical conduit and in close proximity with the end opposite said first end of said cannulation cylinder so as to prevent continuous fluid communication through the annulus defined between the outer surface of said cylindrical conduit and the inner surface defined of said cannulation cylinder.

11. The access device of claim 10 wherein the rearward face of said cylindrical seal is a frusto-conical surface which facilitates the funneling insertion of said cylindrical conduit within said cannulation cylinder during manufacture of said access device.

12. The access device of claim 10 wherein the longitudinal displacement between the rearward face of said end opposite said first end of said cannulation cylinder and of said cylindrical seal defines a seal cavity which reduces shearing of the material of which said cylindrical seal is made.

* * * * *